United States Patent [19]
Brown et al.

[11] Patent Number: 5,430,161
[45] Date of Patent: Jul. 4, 1995

[54] EPOXIDATION USING HYDROGEN PEROXIDE AND TUNGSTEN CATALYSTS

[75] Inventors: Scott W. Brown, Standish; Anthony Hackett, Warrington; Alexander Johnstone, South Wirral; Robert A. W. Johnstone, Wirral, all of United Kingdom

[73] Assignee: Solvay Interox Limited, Warrington, England

[21] Appl. No.: 170,213

[22] PCT Filed: Jun. 25, 1992

[86] PCT No.: PCT/GB92/01154

§ 371 Date: Dec. 28, 1993

§ 102(e) Date: Dec. 28, 1993

[87] PCT Pub. No.: WO93/00338

PCT Pub. Date: Jan. 7, 1993

[30] Foreign Application Priority Data

Jun. 29, 1991 [GB] United Kingdom ............... 9114127

[51] Int. Cl.$^6$ .................. C07D 301/12; C07D 303/04
[52] U.S. Cl. ................................ 549/531; 502/150; 549/546
[58] Field of Search ........................... 549/531

[56] References Cited

U.S. PATENT DOCUMENTS

| | | | |
|---|---|---|---|
| 2,833,787 | 5/1958 | Carlson et al. | 549/531 |
| 4,731,482 | 3/1988 | Venturello et al. | 549/531 |
| 5,274,140 | 12/1993 | Venturello et al. | 549/531 |
| 5,286,885 | 2/1994 | Goetz et al. | 549/531 |

*Primary Examiner*—Joseph E. Evans
*Attorney, Agent, or Firm*—Larson and Taylor

[57] ABSTRACT

Alkenes can be expoxidized with hydrogen peroxide using a homogeneous heavy metal catalyst, but discharge of spent reaction mixtures releases the heavy metal in the environment. The problem can be ameliorated by selecting a heterogeneous catalyst system comprising a tungsten-containing heteropolyacid supported on selected Group IIa, IIb, IVa or IVb inorganic supports or on a strong basic resin, which catalyst has either been calcined after impregnation of in the impregnation stage an alcoholic solution of the heteropolyacid is employed and by employing a nitrilo or oxygenated polar solvent reaction medium. A number of preferred heteropolyacids satisfy the empirical formula $M_{3/n}PW_wMo_{12-w}O_{40}$ in which w represents an integer of at least 1, M represents a counterion and n its basicity. Preferred supports include activated alumina, calcined at 400° to 600° C. and cross-linked quaternary ammonium-substituted polystyrene resins. The most preferred catalysts are made by impregnating an inorganic support with a methanol solution of the heteropolyacid to a desired loading of active material on the support and subsequently calcining the loaded support at 400° to 600° C. Preferred reaction media include acetonitrile and tertiary butanol.

24 Claims, No Drawings

EPOXIDATION USING HYDROGEN PEROXIDE AND TUNGSTEN CATALYSTS

The present invention relates to a process for epoxidation, and more particularly to such a process employing hydrogen peroxide and catalysed by a metal. The invention further relates to metal catalysts which are suitable for use in such epoxidation processes and the production of such catalysts.

In a well known process for epoxidising an olefinic group of formula $>C=C<$ in a substrate to an epoxide of formula

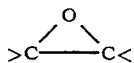

the substrate is reacted with hydrogen peroxide in a suitable reaction medium which often comprises an halogenated hydrocarbon, in which a heavy or transition metal catalyst is dissolved. Such a reaction employs the catalyst homogeneously, which can be very effective because it enables the catalyst to contact the substrate intimately throughout the liquid reaction medium, but as a result the reaction mixture is contaminated by the presence of such metals. In the past, the cheapest method of disposal of spent reaction mixtures or extracts therefrom containing such catalysts comprised their discharge into municipal sewage systems or into watercourses. Such means of disposal, however, are being tolerated to an ever decreasing extent in Western Europe, America and Japan as controls on discharges in to the environment are generally tightened, and in any event such disposal is wasteful of the metal. The metals are dissolved in the reaction mixture, so that their removal from the mixture, possibly for future recycle or re-use, may often be neither a simple nor cheap proposition.

From an environmental viewpoint, it would be desirable for a heavy metal catalyst to be incorporated in a distinctly separate and separable phase from the remainder of the reaction mixture, for example by supporting the catalytic material on a substantially insoluble solid support. However, there are a number of potential difficulties to be overcome to translate a theoretical possibility into a practical reality, pre-eminent amongst which there is the question of whether the catalyst would continue to function. The act of supporting the catalyst transforms any catalyst from a homogeneous to a heterogeneous system. It has been observed that apparently the same catalyst can perform differently in homogeneous and heterogeneous systems under the same general reaction conditions in attempting a desired reaction such as epoxidation. Thus, there is real doubt as to whether the catalyst would be able to perform if a truly heterogeneous system is employed.

A number of explanations may be advanced as to why a different outcome may arise. For example, it may be asserted that the local environment of the catalyst is different in a homogeneous system from that in a heterogeneous system. In the former, the catalyst is dissolved in and therefore dispersed in intimate contact with reactants and solvent throughout the liquid medium, whereas in the latter, the reaction typically takes place at the interface between the catalyst and the liquid phase of the reaction mixture in the immediate vicinity of the support surface. The presence of support can influence the ease with which the reactants can meet and react, and the surface of the support may even promote alternative reactions with one or other of the reactants or intermediates. Moreover, interactions between the catalyst and its support during production of the supported catalyst may modify both. The possible differences in outcome are such that the skilled man cannot predict with any real certainty how to create a heterogeneous system employing heavy or transition metals for the same reaction, and in particular for an epoxidation reaction, starting from homogeneous systems.

On the other hand, if the system created is not truly heterogeneous, in that the catalyst is not firmly attached to the support, it can leach into the reaction mixture during the course of the reaction, so that the reaction still suffers from the waste disposal problems of the catalyst metal in the spent reaction mixture.

It has previously been suggested in U.S. Pat. No. 2,870,171 (Gable) assigned to Shell Development Co that catalysts suitable for conducting epoxidation reactions can be made by depositing tungstic acid compounds on inert adsorptive supports, which ameliorate to a certain extent the problems of discharge of heavy catalytic metals into the environment, but significant concentrations of heavy metals can continue to leach out from the Gable catalyst. It remains desirable, therefore, to locate means which can further reduce the extent of heavy metal leaching but which do not thereby impair the effectiveness or selectivity of the catalytic system.

It has also been suggested in DE-A-2 752 626 by Ugine Kuhlmann in a process for epoxidation in which the aqueous phase is removed continuously during the reaction, that certain heavy metal complexes such as molybdenum acetyl acetonate present as the catalyst could be supported on a carrier. Additionally, Montedison spa in EP-A-0 109 273 have described the preparation of certain peroxytungsten species for use as epoxidation catalysts and their optional simple absorption from an aqueous medium onto a support for the same purpose.

In the course of the present investigations into cataylytic epoxidation systems, it has been found that the effectiveness and/or environmental acceptability of supported cataysts systems can be improved by altering the methods of preparing the cataysts.

According to one aspect of the present invention there is provided a process for epoxidising an olefinic group of part formula $>C=C<$ in a substrate in which the substrate and hydrogen peroxide are brought into and maintained in contact in an organic reaction medium until at least some epoxide has formed in the presence of a heavy metal catalyst supported on a solid support which process is characterised a) by employing a catalyst comprising a tungsten-containing heteropolyacid which is supported on an inorganic solid support selected from a Group IIa, IIb, IIIb, IVa or IVb non-sintered oxide, phosphate or silicate or an organic support selected from strong basic resins, which catalyst was calcined at a temperature of over 300° C. after impregnation of the support with a solution of the heteropolyacid and/or during preparation of the catalyst, the support was impregnated with the heteropolyacid in alcoholic solution and b) by employing a reaction medium comprising a nitrilo and/or an oxygenated polar solvent, and after the reaction has continued for a suitable period the supported catalyst is physically separated from the reaction mixture.

For the avoidance of doubt, the division herein of the Elements of the Periodic Table into Groups a and b is that employed by F. A. Cotton and G. Wilkinson in Advanced Inorganic Chemistry (2nd edition) published by Interscience (John Wiley & Sons).

In related aspects of the present invention, there are provided epoxidation catalysts and a process for preparing an epoxidation catalyst in which a solid particulate support is impregnated by contact with a solution of a tungstic acid compound, is separated from spent solution and is dried characterised in that the tungstic acid compound comprises a tungsten-containing heteropolyacid and the support comprises an inorganic solid support selected from a Group IIa, IIb, IIIb, IVa or IVb non-sintered oxide, phosphate or silicate or an organic support selected from strong basic resins, and in which process the solution of the heteropolyacid employed is alcoholic and/or the impregnated support is calcined at a temperature of over 300° C.

By the use of a catalyst that has been selected or preapred in accordance with the present invention, it is possible to epoxidise the substrate without substantial release of metal into the liquid phase of the reaction mixture based on the selected reaction medium. The solid catalyst can be separated from the reaction mixture by known physical methods, such as centrifugation or filtration, so that the problems associated with the disposal of metal-contaminated effluents are significantly ameliorated. The measure of success of the present invention which employs an heterogeneous catalyst system is that it is able to combine the capability of certain tungsten-containing systems to catalyse the epoxidation reaction at the same time as ameliorating the effluent disposal problems that are associated with the use of homogeneous systems.

It will be recognised that the present invention resides in a combination of features, including the selection of appropriate heteropolyacids, the selection of appropriate supports for those heteropolyacids, the method of producing the supported catalysts and in some aspects the use of such supported catalysts in an appropriate reaction medium. Consequently, in a further aspect of the present invention, there is provided a reaction medium in which epoxidation reactions can be conducted which comprises a nitrilo and/or an oxygenated polar solvent in which is dispersed a particulate catalyst system comprising a tungsten-containing heteropolyacid which is supported on a solid inorganic support selected from Group IIa, IIb, IIIb, IVa or IVb non-sintered oxide, phosphate or silicate or on an organic support selected from strongly basic resins which catalyst has been calcined or prepared using an alcoholic impregnating solution.

A number of other supported heteropolyacid-based systems have been tested for epoxidising the same substrates with inferior results. Thus, by way of example, processes employing different catalyst systems in which the invention selection of heteropolyacids had been incorporated on to different supports or aqueous impregnated supports have not been calcined and processes employing a different reaction medium have suffered from one or more of the disadvantages of impaired selectivity of conversion of the substrate to the epoxide, or of markedly increased leaching of the heteropolyacid into the reaction mixture.

Preferably, the catalyst contains phosphorus as the non-metallic heteroatom.

Although tungsten may constitute the entire metallic component of the heteropolyacid, at least one other transition metal may be incorporated therein. One preferred transition metal co-component is molybdenum. Many particularly preferred heteropolyacids for employment in the present invention process and reaction medium can be represented by the empirical formula $M_{3/n}PW_wMo_{12-w}O_{40}$ when they are brought into contact with the support in which w represents an integer of at least 1 and preferably at least 6. In a number of instances, noteworthy results have been obtained when w represented either 6 or 12. M represents hydrogen or like counterion, and n is its basicity in the general formula. It is believed that the supported catalyst retains its empirical ratio of tungsten to phosphorous and molybdenum, but that the interaction of the catalyst with the surface of the support may result in the catalyst becoming bonded chemically to the support, thereby modifying both the catalyst itself and the support surface. Such treatments may also encourage a redistribution of the metal between species of different nuclearity.

Other heteropolyacids contemplated for use in the present invention include those containing at least one first series transition metal, including specifically iron, manganese, cobalt and nickel, for example in heteropolyacids of the formula $M_{(7-v)/n}PW_{11}M_xO_{36+v}$ in which Mx represents the other transition metal, v is its oxidation state and M is the counterion of basicity n as before.

The support for the heteropolyacid catalyst is selected from solids of Group IIa, IIb, IIIb, IVa and IVb elements and from organic basic ion exchange resins. Within the class of Group IIa compounds, it is often convenient to select as support from magnesium compounds, including in particular, magnesium oxide and magnesium silicate. Within the class of group IIb compounds, it can be convenient to select from zinc compounds as support, including specifically zinc oxide. Within the class of Group IVa compounds, it is often convenient to select from titanium or zirconium compounds, including specifically titanium oxide and zirconium phosphate. From within the class of inorganic Group IVb compounds, it is often desirable to select as supports from tin compounds, many of which are readily available, or from germanium compounds. Specific examples include tin oxide.

In a number of preferred embodiments, the catalyst support is selected from Group IIIb compounds, especially from non-sintered oxides, and particularly from aluminium compounds. An especially suitable support comprises an activated alumina, including in particular, gamma alumina. For the avoidance of doubt, the term activated alumina refers to non-sintered alumina obtainable by calcining alumina or aluminium hydroxide at temperatures below that at which sintering occurs, and includes specifically the products obtained by calcining at around 400° to 600° C. The alumina may already be present in the activated form at the time of contact with the catalyst or alternatively neutral alumina or aluminium hydroxide may be converted into activated alumina by a post-impregnation calcination step.

The organic support can be selected from strong base ion exchange resins, of which a typical resin comprises a crosslinked polystyrene, the cross linking monomer often comprising divinylbenzene in a small fraction of the monomer mix such as 1 to 2 mole %, the benzene nucleus in the styrene being substituted by an organic base, particularly by an alkyleneammonium group. Examples of suitable ammonium groups include alkylenetrialkylammonium, often methylenetrimethylammonium or the corresponding groups in which one or more of the methyl groups are replaced by another short chain alkyl such as ethyl and/or one of the alkyl groups being hydroxyl-substituted, as in methylenedimethylhydroxyethylammonium group. Other suitable anion exchange resins include insoluble polyacrylic resins in which the carboxylic acid function is further substituted by an alkyleneammonium group, for example ethylenetrimethylammonium. The ion-exchange resin can be selected from micro or macro-reticulated strongly basic resins. Naturally, the invention does not encompass so calcining any organic resin after impregnation with the heteropolyacid solution that it is structurally harmed, The support is usually employed in the form of discrete particles, the particle size range often being selected such that the supported catalyst particles are distributed: through the reaction mixture to a substantial extent during the agitation of the mixture. A convenient average particle size often lies in the range of from about 100 microns to about 5 mm.

The catalyst can be introduced to the support most conveniently in solution in a suitable solvent, which can comprise water or a polar organic solvent such as a low molecular weight aliphatic alcohol or a mixture thereof. Low molecular weight herein indicates up to C4 (butanols), as in the subsequent epoxidation reaction medium. The solution can, in principle, contain any concentration of catalyst up to and including a saturated solution, and in preference is at or near saturation, so as to minimise the volume of solvent that is subsequently removed. The solution can be contacted with the support in bulk until a desired amount has been absorbed and after separation from the liquid phase, the impregnated support is thereafter dried and can then be calcined. Calcination is an optional, though highly preferred stage if an alcoholic impregnation stage has been employed, but is an essential stage if simply an aqueous impregnation stage is employed. The impregnation contact period often lasts from about 30 minutes to 8 hours. In a variation, the support may be charged into a column through which a solution of the heteropolyacid is permitted to percolate, preferably with recycle of the eluate to maximise uptake of the catalyst from the solvent.

The contact may be made at or around ambient temperature, which is typically in the region of from about 15° to 25° C. or it may be conducted at an elevated temperature up to the boiling point of the solvent under the selected pressure conditions. By employing an elevated temperature, and particularly one that is within 10° C. of the solvent boiling point, the solvent is evaporated away to at least some extent during the contact period. Once the solution has reached saturation, any further solvent removal results in the catalyst being deposited on the support. Accordingly, the support can thereby be loaded with a higher level of catalyst than is obtainable by simply impregnating the support with a saturated solution, separating the support from excess liquor and drying. Particularly for use in conjunction with solvent evaporation during the contact phase, the solvent is methanol or an alternative low boiling point solvent.

The extent of loading of the catalyst is to at least some extent at the discretion of the user. It is often convenient or desirable to employ a loading of from 4 to 30% by weight of the catalyst, calculated as the metal, based on the dry weight of the support. In a number of effective embodiments the catalyst loading is between 5 and 17% by weight of the dry weight of the support.

During calcination of the supported catalyst material which has been obtained by impregnation of an inorganic support with the heteropolyacid, it is believed that formation of a bond between the catalyst and the support is promoted, which can assist in controlling the leaching of catalyst into the reaction mixture. However, as a result of such interaction and bond formation, the catalyst species may be altered to some extent by such calcination, so that the value of such a post impregnation calcination tends to vary depending upon the support employed. For some supports, including alumina in particular, it is advantageous to calcine at a temperature of at least 300° C. and usually not higher than about 600° C. In a number of instances, a particularly suitable temperature for post-impregnation calcination of for example alumina is at least about 400° C. and especially from about 450° to about 550° C. Other supports for which post impregnation calcination is an appropriate activity include magnesium silicate and zirconium phosphate. However, when magnesium oxide or a related oxide such as calcium or zinc is employed as support, it is preferable not to calcine the support after it has been impregnated by the heteropolyacid catalyst.

The epoxidation process in many embodiments is conveniently carried out in an organic polar solvent, which in particular can comprise either acetonitrile or a low molecular weight aliphatic alcohol preferably selected from ethanol, or a propanol, particularly isopropanol or a butanol such as tertiary butanol or mixtures thereof. Higher molecular weight alcohols such as a pentanol or hexanol which are liquid at the epoxidation reaction temperature may be employed as at least part of the medium. In some instances, it is possible to select a combination of relatively mild catalyst and/or reaction conditions when employing methanol as solvent, though under less mild conditions employing a catalyst containing a higher proportion of tungsten, further inter-reaction of methanol with epoxide to form a methoxy-hydroxy compound has been observed.

The invention process is applicable to epoxidising alkenes containing a wide range of variations in for example the nature and size of the substrate molecule, the location of and number of olefinic group or groups within the molecule, and the extent of substitution. The substrate may be classifiable as aliphatic, cycloaliphatic or aromatic, depending on the nature of its non-olefinic moiety. That moiety can, if desired, contain at least one heteroatom embedded in its structure, which is often selected from nitrogen, sulphur and oxygen. The main chain or the nucleus can be substituted by at least one alkyl, aryl or cycloalkyl side chains. The moiety can be substituted in the main chain, nucleus or side chain by one or more substitutents which are considered to be sufficiently inert during the epoxidation reaction, selected from halogen groups, particularly chloro, bromo or fluoro groups, hydroxy, alkoxy, nitro, amino, carbonyl, nitrile, and carboxylic acid, ester or amide groups. The substrate, in general, contains from 2 to about 40 carbons and in many instances from 3 to about 12 carbons. The olefinic group or groups may be terminal or embedded in the structure.

In many embodiments of the invention, the process employs alkenes in accordance with the following general formula:

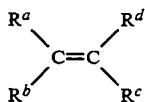

in which $R^a$, $R^b$, $R^c$, and $R^d$ are the same as or different from each other, and each represents either hydrogen or a substituent selected from (i) $R^x$ which is selected from halo substituents, particularly chloro, bromo or fluoro groups, and from carboxylic acid, ester and amide groups, and (ii) alkyl, cycloalkyl or aryl groups which themselves may be substituted by $R^x$ and/or optionally carry at least one alkyl cycloalkyl or aryl or side chain itself optionally substituted by $R^x$ and/or contain at least one heteroatom within its chain or nucleus structure.

Alkenes which can be contemplated in the present invention include: but-1-ene, but-2-ene, isobutene, butadiene, the pentenes and notably isoamylene, piperylene, the 1-, 2- and 3-hexenes, the hexadienes, hept-1-ene,3-ethylpent-2-ene, oct-1-ene, diisobutylene, 2,4,4-trimethyl pent-1-ene and -2-ene, non-1-ene, undec-1-ene, dodec-1-ene, tridec-1-ene, tetradec-1-ene, pentadec-1ene, hexadec-1-ene, heptadec-1-ene, octadec-1-ene, nonadec-1-ene, eicos-1-ene, the trimers and tetramers of propylene, the polybutadienes, isoprene and the terpenes such as the terpinenes, limonene, terpinolene, sabinene, pinene, camphene, myrcene, cadinene, cedrene, santalene, calarene, colophene and the polyterenes as well as their derivatives such as geraniol, linalol and linalyl acetate, methylenecyclopropane, cyclopentene, cyclopentadiene, cyclohexene, methylenecyclopentane, methylenecyclohexane, norbornene, cycloheptene, vinylcyclohexane, vinylcyclohexene, styrene, cyclooctene,the cyclooctadienes, vinylnorbornene, indene, tetrahydroindene, alpha-methylstyrene, dicyclopentadiene, divinylbenzene, cyclododecene, cyclododecatriene, stilbene, diphenylbutadiene, vitamin A, beta-carotene, vinylidene fluoride, allyl chloride and bromide, the trichloropropylenes, crotyl chloride, methallyl chloride, the dichlorobutenes, allyl alcohol, methallyl alcohol, but-2-ene-ol, but-2-ene diol, the cyclopentene diols, 4-pentenol, 2-methylpent-2-ene-1-ol, 1,2-dihydroxy-4-vinylbenzene, 2,7-octadien-1-ol, cyclohexenylcarbinol, tridec-2-ene-1-ol, the unsaturated steroids, ethoxyethylene, isoeugenol, anethole, isosafrole, the unsaturated carboxylic acids of all types such as acrylic acid, methacrylic acid, crotonic acid, maleic acid, vinylacetic acid and the unsaturated fatty acids including more particularly oleic, linoleic, palmitoleic, linolenic, vaccenic, gadoleic, ricinoleic and eleostearic acids and the natural fats and oils which contain them as well as the esters of these unsaturated acids such as the alkyl acrylates and methacrylates, diallyl maleate, methyl-7-hydroxy-5-heptenoate, methyl oleate and the esters of unsaturated alcohols such as allyl carbonate, diallyl phthalate, allyl acetate.

It will be recognised that to at least a certain extent, the selection of a preferred catalyst system from amongst the systems contemplated in the present invention takes into account the substrate which it is desired to epoxidise. Thus, for example, supported phosphopolytungstic acid catalysts and particularly those that have been calcined, have shown particular application in the epoxidation of cycloalkenes, such as cyclohexene to cyclooctene, and alkylsubstituted cycloalkenes.

The epoxidation reaction is often conducted at an elevated reaction temperature of from 50° C. up to the reflux temperature of the reaction medium, and particularly from 60° to 85° C. Particularly for substrates which boil under standard atmospheric pressure at lower temperatures than the desired reaction temperature, the reaction may be conducted at an elevated pressure selected so at to permit the desired temperature to be attained, but of course the higher boiling substrates may likewise be reacted at elevated pressure if desired.

It is desirable to bring the substrate into contact with at least half the stoichiometric amount of hydrogen peroxide for epoxidation, ie at least 0.5 mole of hydrogen peroxide per mole of substrate if the latter contains a single olefinic group and normally not more than 10 moles hydrogen peroxide per mole of substrate. In many instances, a mole ratio of from 1:1 to about 3:1 hydrogen peroxide to substrate is employed, on the same basis.

The hydrogen peroxide is preferably introduced into the reaction mixture in the form of a concentrated aqueous solution, and frequently of from about 35 to 70% w/w hydrogen peroxide. Preferably, the hydrogen peroxide is introduced into the reaction mixture which contains both the substrate and catalyst system, and particularly preferably it is introduced gradually, for example over a period of from 30 minutes to 4 hours.

The ratio of supported catalyst to substrate can be selected over a wide range of weight ratios, often in the range of from 1:10 to 1:160 and in a number of instances from 1:25 to 1:75. The ratio chosen can take into account the loading of catalyst on the support and the activity of the substrate, as well as the other reaction conditions selected.

The volume of reaction medium employed is often selected in the range of from 1 to 10 volumes of solvent per volume of substrate and in many instances within the range of from 3/2 to 3 volumes of solvent per volume of substrate.

The overall reaction period, including the period of introduction of the second reagent which is normally hydrogen peroxide, often comprises from about 2 to about 10 hours, and in many instances is from about 3 to about 7 hours. However, longer reaction periods of for example 10 to 30 hours can be employed, if desired by the user.

When the epoxidation process has been permitted to continue for the desired period, the reaction can be halted by physically separating the particulate catalyst from the reaction mixture by filtration or centrifugation and/or by cooling the mixture for example to ambient. It has been found that the invention catalyst system does not leach into the reaction medium to any significant extent under the reaction conditions described hereinbefore. Confirmatory measurements in some trials indicated that no more than about 1–2% of the heavy metal in the heteropolyacid catalyst had leached out, though, naturally, the precise loss into solution will tend to vary, depending upon the particular catalyst/support combination and the conditions in which the epoxidation reaction is conducted. However, as a consequence of such retention of the catalyst on the support, it may be deduced that the invention meets the objective of ameliorating to a significant extent the problems caused by the presence of heavy metal contaminants in the reaction mixture at the end of the reaction. Moreover, the recovered catalyst can be reemployed in a further reaction mixture, possibly after washing with solvent and/or drying and/or re-calcination, if desired.

A further advantage of the invention process is that as a result of the selection of reaction medium, the reaction can avoid the use of chlorinated hydrocarbons as solvents which are themselves viewed with increasing disfavour by regulatory and Health and Safety Authorities.

Having described the invention in general terms, specific embodiments thereof are described in greater detail by way of example only.

PREPARATION OF THE SUPPORTED CATALYSTS

The inorganic supported catalysts employed in the Examples were made by one or other of the two general methods or variations thereof.

In general method A, the selected heteropolyacid (15 g) was dissolved in demineralised water (600 ml). The selected particulate support (100 g) was then mixed with the heteropolyacid solution at ambient temperature of about 22°/23° C. for 4 hours. The solids were filtered off and washed with a small volume of demineralised water and then dried overnight in an oven set at 60° C. The dried solid was calcined at a selected temperature for 4 hours in a muffle furnace.

In general method B, the heteropolyacid catalyst (2 g) was dissolved in methanol (50 g), at 60° C. approx, ie hot, for catalyst V and at ambient, ie about 22° C. for catalyst XI and the resultant mixture was contacted with the selected support (25 g) and sparged with nitrogen at ambient in order to remove the solvent and thereby deposit the catalyst on the support. Residual traces of solvent were removed in a rotary evaporator. Thereafter the supported catalyst was calcined for 4 hours at the selected temperature, as in method A.

The conditions for the preparation of the inorganic supported catalyst systems are summarised in Table 1 below. The expression a-alumina means alpha alumina and g-alumina indicates gamma alumina. Catalyst R6 is unsupported phosphotungstic acid which was employed as the impregnation species onto many of the supports listed in Table 1. CP in catalyst V represents cetyl pyridinium.

TABLE 1

| Catalyst Ref. | Impregnation Species | Support | Prep Method | Calcine Temp °C. |
|---|---|---|---|---|
| I | $H_3PW_{12}O_{40}$ | g-$Al_2O_3$ | A | 500 |
| II | $H_3PWMo_{11}O_{40}$ | " | A | 500 |
| III | $H_3PW_{12}O_{40}$ | neutral $Al_2O_3$ | A | 500 |
| IV | " | Mg silicate | A | 500 |
| V | $(CP)_3PW_{12}O_{40}$ | g-alumina | B | 500 |
| VI | $H_3PW_{12}O_{40}$ | g-$Al_2O_3$ | A | 600 |
| VII | " | " | A | 400 |
| VIII | " | " | A | 200 |
| IX | " | " | A | — |
| X | " | " | A | 500 |
| XI | " | " | B | 500 |
| XII | " | $ZrPO_4$ | A | 500 |
| XIII | " | $SnO_2$ | A | 500 |
| XIV | " | $Al(OH)_3$ | A | 500 |
| XVI | " | $TiO_2$ | A | 500 |
| XVII | $H_3PW_6Mo_6O_{40}$ | a-alumina | A | 500 |
| R1 | $H_3PMo_{12}O_{40}$ | $SiO_2$ | A | 500 |
| R2 | $H_3PW_{12}O_{40}$ | acid-$Al_2O_3$ | A | 500 |
| R3 | " | basic-$Al_2O_3$ A | | 500 |
| R4 | " | a-alumina | A | 500 |

TABLE 1-continued

| Catalyst Ref. | Impregnation Species | Support | Prep Method | Calcine Temp °C. |
|---|---|---|---|---|
| R5 | " | H-mordenite A | | 500 |
| R6 | " | not supported | | |

The organic resin-supported catalyst, XV, was made by a variation of method A, in which particulate resin (strongly heteropolyacid ($H_3PW_6Mo_6O_{40}$, 1.14 g) in water (7.2 ml) was basic resin available under the trademark AMBERLYST 26,2 g) was introduced into a glass tube and a solution of the percolated through, collected and recycled four times. The resin was thoroughly water washed until the washings were colourless and around pH5, then washed with acetone and dried under vacuum at 50° C. for 2 hours.

EXAMPLES 1 TO 8 AND COMPARISONS C9 TO C14

In these Examples and Comparisons, the selected catalyst (0.5 g of as made catalyst/support), substrate (cyclohexene, 2 g except in Ex 3, Ex4, Ex7 and C11, C15 which each employed 8 g) and solvent (40 ml) were charged into a three-necked glass reaction vessel equipped with a water-cooled condenser and the stirred mixture was heated to reflux temperature, which was about 80° C., except in Example 2, where it was about 60° C. Aqueous hydrogen peroxide solution (35% w/w except in Ex3 which used 70% w/w) was introduced slowly into the stirred refluxing reaction mixture over a period of 45 minutes to 1 hour. The mixture was refluxed for a further 5 hours. The reaction mixture was then analysed by gas liquid chromatography to determine how much substrate had been consumed during the reaction, including evaporation losses, and which reaction products had been produced and in what proportions. In some instances, the available oxygen in the reaction mixture was also measured by a conventional iodide/thiosulphate method to determine what proportion of the hydrogen peroxide had been consumed.

In Comparison C14, the reaction was conducted in the presence of same weight of both the catalyst and the gamma alumina as present in the supported catalyst I, but the two materials were introduced separately.

The results are summarised in Table 2 below. A — indicates that none of the designated product was detected, and * indicates that the epoxide had been further reacted to the monomethoxy ether derivative. The term Mole Ratio refers to the mole ratio of substrate to hydrogen peroxide. The term % Conv indicates the molar proportion of substrate which was consumed during the reaction period, either by reaction or by other means. The term % Selectivity indicates the molar proportion of the amount of substrate consumed which was present as the specified product, viz the epoxide or the 1,2 diol. The term "Catalyst EPG" indicates the number of millimoles of epoxide product produced per g of catalyst-/support.

TABLE 2

| Ex. No | Cat Ref | Solvent | Mole Ratio | Substrate % Conv | % Selectivity Epoxide | % Selectivity Diol | Catalyst EPG |
|---|---|---|---|---|---|---|---|
| 1 | I | t-BuOH | 1:2 | 31 | 47 | 5 | 7.0 |
| 2 | I | MeCN | 1:2 | 67 | 15 | — | 5.5 |
| 3 | I | t-BuOH | 1:2 | 53 | 32 | 6 | 34 |

TABLE 2-continued

| Ex. No | Cat Ref | Solvent | Mole Ratio | Substrate % Conv | % Selectivity Epoxide | % Selectivity Diol | Catalyst EPG |
|---|---|---|---|---|---|---|---|
| 4 | I | MeOH | 1:2 | 47 | *22 | — | *20 |
| 5 | II | t-BuOH | 1:2 | 41 | 9 | — | 1.7 |
| 6 | III | t-BuOH | 1:1 | 39 | 12 | — | 9.6 |
| 7 | IV | T-BUOH | 1:1 | 32 | 7 | — | 4.1 |
| 8 | V | t-BuOH | 1:2 | 40 | 27 | — | 5.2 |
| C9 | R1 | t-BuOH | 1:2 | 98 | — | 19 | 0 |
| C10 | R2 | t-BuOH | 1:2 | 55 | — | 19 | 0 |
| C11 | R3 | t-BuOH | 1:2 | 42 | 1 | 11 | 0.9 |
| C12 | R4 | t-BuOH | 1:2 | 66 | — | 20 | 0 |
| C13 | R5 | t-BuOH | 1:2 | 44 | — | 17 | 0 |
| C14 | R6 | t-BuOH | 1:2 | 85 | — | 36 | 0 |

From Table 2, it can be seen that the selection of the calcined catalyst, the selection of the support and the selection of the solvent are all important aspects in producing a heterogeneous epoxidation process. In particular, it will be observed from Comparisons C9 to C13 that the combination of a suitable catalyst with a different support results in markedly impaired epoxidation compared with Example 1, even though a substantial conversion of the substrate occurred. From Comparison C14, it can be seen that the unsupported catalyst, even in the presence of the catalyst support, did not result in significant epoxide product compared with the result when the two components are brought together in a preliminary step.

EXAMPLES 15 TO 19

In these Examples, the process of Example 1 was repeated, employing the catalysts specified in Table 3 below, which differ from each other in the temperature at which the impregnated support was calcined after drying and t-butanol as the solvent.

TABLE 3

| Ex. No | Catalyst | Calcine Temp °C. | Substrate % Conv | % Selectivity Epoxide | % Selectivity Diol | Catalyst EPG |
|---|---|---|---|---|---|---|
| 15 | VI | 600 | 48 | 27 | 3 | 6.4 |
| 16 | I | 500 | 31 | 47 | 5 | 7.0 |
| 17 | VII | 400 | 71 | 16 | 3 | 5.4 |
| C18 | VIII | 200 | 66 | 4 | 6 | 1.4 |
| C19 | IX | — | 48 | 14 | 10 | 3.3 |

From Table 3 it can be seen that the most effective catalyst system was obtained when the aqueous-impregnated supported catalyst had been calcined at a temperature of about 400° C. or higher.

EXAMPLES 20 AND 21

In these Examples, Example 1 was repeated, the catalyst that was recovered by filtration from the reaction mixture of Example 20 being employed as catalyst in Example 21. The concentration of dissolved tungsten in the reaction mixture was measured at the end of the reaction period from which the total amount of W that had leached into solution was calculated and expressed as a percentage of the tungsten that was present in the catalyst employed. The results are summarised in Table 4 below.

TABLE 4

| Ex. No | Catalyst | % of W Leached | Substrate % conv | % Selectivity Epoxide | % Selectivity Diol | Catalyst EPG |
|---|---|---|---|---|---|---|
| 20 | I | <1% | 44 | 20 | 3 | 4.2 |
| 21 | I | <1% | 46 | 17 | 9 | 3.3 |

Subsequent repetition of this method of catalyst recycling with like prepared catalysts has shown that the catalyst productivity (EPG) was maintained substantially unchanged after 5 recyclings.

EXAMPLES 22 TO 25

In these Examples, the process of Example 1 was repeated, but employing cyclooctene as the substrate and catalytic materials containing the loadings of tungsten specified in Table 5. In Example 25, the higher amount of substrate, 8 g, was employed.

TABLE 5

| Ex. No | Catalyst Ref | Tungsten Loading % w/w | Substrate % Conv | % Selectivity Epoxide | Catalyst EPG |
|---|---|---|---|---|---|
| 22 | I | 3.6 | 28 | 64 | 6.2 |
| 23 | X | 7.8 | 50 | 70 | 13 |
| 24 | XI | 15.6 | 82 | 86 | 26 |
| 25 | XI | 15.6 | 87 | 80 | 101 |

From Table 5, it can be seen that increasing the loading of phosphotungstic acid on the gamma alumina support resulted in significantly improved productivity for the catalyst at epoxidising cyclooctene. It was also observed that the consumption of hydrogen peroxide in the Examples was respectively 100%, 99%, 51% and 42%. It may therefore be deduced that the process of Examples 24 and 25 employing catalyst ref XI employed especially advantageous conditions.

EXAMPLES 26 TO 31

In these Examples, the process of Example 22 was followed, employing the catalysts and reaction media designated in Table 6 below.

TABLE 6

| Ex. No | Catalyst Ref | Solvent | Substrate % Conv | % Selectivity Epoxide | Catalyst EPG |
|---|---|---|---|---|---|
| 26 | XI | t-BuOH | 95 | 79 | 27 |
| 27 | XI | MeCN | 98 | 89 | 32 |
| 28 | XI | iPrOH | 64 | 92 | 21 |
| 29 | XII | t-BuOH | 46 | 81 | 14 |
| 30 | XIII | t-BuOH | 81 | 39 | 12 |
| 31 | XIV | t-BuOH | 26 | 39 | 3.7 |

From Table 6, it can also be seen that the epoxidation reaction takes place in isopropanol and that the best results were obtained using acetonitrile with those in tertiary butanol also being very good. In addition, the Examples demonstrate the effectiveness for epoxidation of phosphotungstic acid catalysts supported on zirconium phosphate or tin oxide or aluminium hydroxide that is subsequently calcined at an activating temperature.

EXAMPLE 32

In this Example, Example 27 was repeated but using 1-octene instead of cyclooctene. 41% of the substrate was converted, the selectivity to epoxide was 20% and the catalyst productivity was 2.8.

EXAMPLE 33

In this Example, 1-methylcyclohexene (0.5 g) and resin supported catalyst XV (0.42 g) in methanol (25 ml) were heated to 60° C. and concentrated hydrogen peroxide (70% w/w, 1.52 g) was introduced over a short period. The stirred mixture was maintained at reflux until no alkene was detectable, after about 30 hours. Analysis of the reaction products indicated that approximately 20% of the substrate had been converted to epoxide, and approximately 69% to the methoxyhydroxy derivative.

EXAMPLE 34

In this Example, the procedure of Example 1 was followed, but employing catalyst XVI, $TiO_2$ providing the support. Approximately 25% conversion of the substrate was observed at a selectivity of about 53%.

EXAMPLE 35

In this Example, the procedure of Example 1 was followed, but employing catalyst XVII. Approximately 48% conversion was observed, at a selectivity of about 76%.

COMPARISON 36, AND EXAMPLES 37, 38 AND 39

In Comparison 36, a supported catalyst R7 was made in accordance with the general procedure described by Gable in U.S. Pat. No. 2,870,171. Phosphotungstic acid, $H_3PW_{12}O_{40}$, 3.0 g was dissolved in water, 200 ml at ambient temperature and gamma alumina, 20 g, type was mixed in. The resultant slurry was stirred for an hour, and the solids were then filtered and dried in an oven overnight at 50° C. under a mild vaccuum.

In Example 37, for Catalyst XVIII the procedure for making catalyst R7 was repeated, but followed by calcination of the dried solids at 500° C. for 4 hours.

In Example 38, catalyst XIX was made by the same procedure as for Catalyst XI, ie procedure B, for the impregnation of a further sample of the same gamma alumina (20 g) employed in Comparison 36 with phosphotungstic acid, $H_3PW_{12}O_{40}$, 3.0 g in methanol (30 ml) except that it was terminated after the material had been dried, ie the catalyst was not calcined.

In Example 39, catalyst XX was made by the procedure for XIX but followed by calcination for 4 hours at 500° C.

The four catalysts of Comparison 35 and Examples 36 to 38 represent respectively:

| R7 | Comp 36 | aqueous impregnation, no calcination |
|---|---|---|
| XVIII | Ex 37 | aqueous impregnation plus calcination |
| XIX | Ex 38 | alcoholic impregnation, no calcination and |
| XX | Ex 39 | alcoholic impregnation plus calcination. |

The supported phosphotungstic acid catalysts produced in Comparison 35 and Examples 36 to 38 were then employed to catalyse the reaction between hydrogen peroxide and cyclooctene under the process conditions of Example 1 varied by employing 1 g of catalyst instead of 0.5 g and a total reaction time of 4 hours instead of 6 hours. The extent of tungsten leaching was measured as well as the extent of substrate conversion, selectivity to epoxide formation and the productivity of the catalyst (EPG). The results are summarised in Table 7 below, in which bdl indicates below detection limit in the reaction mixture.

TABLE 7

| Ex. No | Substrate % Conv | Epoxide % Yield | Epoxide % Selectivity | Catalyst EPG | Leaching of W mg/l | Leaching of % |
|---|---|---|---|---|---|---|
| C36 | 36 | 26 | 73 | 34 | 26 | 1.5 |
| 37 | 23 | 21 | 91 | 27 | 6 | 0.3 |
| 38 | 40 | 31 | 81 | 49 | 0.5 | 0.03 |
| 39 | 45 | 43 | 96 | 69 | bdl | |

From Table 7, it can be seen readily that the comparison catalyst XVIII had still permitted tungsten to leach into the reaction mixture to a concentration of 26 mg/l by the end of the reaction. The extent of tungsten leaching was ameliorated substantially in Catalyst XIX, demonstrating the beneficial effect of calcination.

By comparing the results using Catalyst XX with XVIII, neither of which had been calcined, it can be seen that impregnating the support with an alcoholic solution of phosphotungstic acid rather than an aqueous solution not only produced a catalyst which was more active, with higher selectivity to epoxide formation, but also resulted in markedly diminished leaching of tungsten into solution. A comparison between Catalysts XXI and XIX, both of which had been calcined, shows a similar comparison to that between Catalysts XVIII and XX. Moreover, a comparison between Catalysts XXI and XX shows that the effect of calcining the alcoholic-impregnated support was to improve substrate conversion, epoxide yield and selectivity as well as reduce the extent of tungsten leaching to impressively low levels.

EXAMPLE 40

In this Example, the general procedure of Example 1 was repeated, using 1 g of catalyst/support no ??? per 8 g of cyclooctene. At the end of the reaction period, the solid catalyst was recovered, water washed and then dried in an oven overnight. The next day, the same epoxidation procedure was repeated, but using the recovered catalyst. The epoxidation results on the third recycle of the catalyst have been compared with those obtained on the first cycle. The extent of substrate conversion fell from 24% to 22% on the third recycle, but the extent of epoxide formation remained unchanged because the selectivity of the process increased from 87 to 96%. Consequently, catalyst productivity remained unimpaired.

What is claimed is:

1. A process for epoxidising an olefinic group of part formula >C=C< in a substrate in which the substrate and hydrogen peroxide are brought into and maintained in contact in an organic reaction medium until at least some epoxide has formed in the presence of a heavy metal catalyst supported on a solid support which process is characterised a) by employing a catalyst comprising a tungsten-containing heteropolyacid which is supported on an inorganic solid support selected from a Group IIa, IIb, IIIb, IVa or IVb non-sintered oxide, phosphate or silicate or an organic support selected from strong basic resins, which catalyst was calcined at a temperature of over 300° C. after impregnation of the support with a solution of the heteropolyacid and/or during preparation of the catalyst, the support was impregnated with the heteropolyacid in alcoholic solution and b) by employing a reaction medium comprising a nitrilo and/or an oxygenated polar solvent, and after the reaction has continued for a suitable period the supported catalyst is physically separated from the reaction mixture.

2. A process according to claim 1 in which the heteropolyacid contains phosphorus as the non-metallic heteroatom.

3. A process according to claim 1 in which the heteropolyacid satisfies the empirical formula $M_{3/n}PW_wMo_{12-w}O_{40}$ when it is brought into contact with the support in which w represents an integer of at least 1 and M represents hydrogen or other counterion and n represents its basicity.

4. A process according to claim 3 in which w in the formula is selected in the range of from 6 to 12.

5. A process according to claim 1 in which the inorganic support is selected from magnesium, zinc, titanium, zirconium, or tin compounds.

6. A process according to claim 5 in which the support is selected from magnesia, magnesium silicate, titania, zirconium phosphate, or tin oxide.

7. A process according to any claim 1 in which the support comprises an activated alumina.

8. A process according to claim 7 in which the support comprises gamma alumina.

9. A process according to claim 1 in which the inorganic supported catalyst is calcined at a temperature of from 300° to 600° C.

10. A process according to any claim 1 in which the support comprises a cross linked ammonium-substituted polystyrene ion exchange resin.

11. A process according to claim 1 in which the catalyst has been made by impregnating the support with a solution of the heteropolyacid in a low molecular weight aliphatic alcohol.

12. A process according to claim 11 in which the low molecular weight aliphatic alcohol is methanol.

13. A process according to claim 1 in which the loading of catalyst calculated as tungsten on the support is from 4 to 30% of the dry weight of the support.

14. A process according to claim 1 in which the solvent in the reaction medium is selected from acetonitrile or a low molecular weight aliphatic alcohol containing from 2 to 6 carbons.

15. A process according to claim 14 in which the solvent comprises acetonitrile or tertiary butanol.

16. A process according to claim 1 which is conducted at a temperature of from 50° C. to the reflux temperature of the reaction mixture.

17. A process according to claim 16 which is conducted at a temperature of from 60° to 85° C.

18. A process according to claim 1 in which at least 0.5 moles of hydrogen peroxide is employed per mole of substrate, calculated as monoolefinic substrate.

19. A process according to claim 18 in which the mole ratio of hydrogen peroxide to substrate is from 1:1 to 3:1, calculated as a monoolefinic substrate.

20. A process according to claim 1 in which the hydrogen peroxide employed has a concentration of at least 35% w/w.

21. A process according to claim 1 in which the reaction is permitted to continue for a period of at least 2 hours.

22. A process according to claim 21 in which the reaction is permitted to continue for 3 to 7 hours.

23. A process according to claim 1 in which the supported catalyst after separation from the reaction mixture is re-employed with a further amount of alkene.

24. A process according to claim 1 in which the alkene has the following general formula:

$$\begin{array}{c} R^a \\ \phantom{R^a} \diagdown \\ \phantom{R^aR^b} C=C \\ \phantom{R^a} \diagup \\ R^b \end{array} \begin{array}{c} R^d \\ \diagup \\ \\ \diagdown \\ R^c \end{array}$$

in which $R^a$, $R^b$, $R^c$ and $R^d$ are the same as or different from each other, and each represents either hydrogen or a substituent selected from (i) $R^x$ which is selected from halo substituents, and from carboxylic acid, ester and amide groups, and (ii) alkyl, cycloalkyl or aryl groups which themselves may be substituted by $R^x$ and/or optionally carry at least one alkyl cycloalkyl or aryl or side chain itself optionally substituted by $R^x$ and/or contain at least one heteroatom within its chain or nucleus structure.

* * * * *